United States Patent [19]

Frost et al.

[11] 4,102,207
[45] Jul. 25, 1978

[54] ELECTROMAGNETIC ULTRASOUND TRANSDUCER

[75] Inventors: Harold M. Frost, Rockville, Md.; Thomas L. Szabo, Boston, Mass.

[73] Assignee: The United States of America as represented by the Secretary of the Air Force, Washington, D.C.

[21] Appl. No.: 751,240

[22] Filed: Dec. 16, 1976

[51] Int. Cl.² ............................................ G01N 29/00
[52] U.S. Cl. ..................................................... 73/643
[58] Field of Search ..................... 73/71.5 US, 67.5 R, 73/67.7, 643; 324/37, 40

[56] References Cited

U.S. PATENT DOCUMENTS

| 3,583,213 | 6/1971 | Houck et al. | 73/67.5 R |
| 3,786,672 | 1/1974 | Gaerttner | 73/71.5 US |
| 3,850,028 | 11/1974 | Thompson et al. | 73/71.5 US |
| 3,918,295 | 11/1975 | Herbertz | 73/71.5 US |

FOREIGN PATENT DOCUMENTS 1,425,201  2/1976  United Kingdom ........... 73/71.5 US

OTHER PUBLICATIONS

Butenko et al., "Electromagnetic-Acoustic Non-Destructive Testing in Soviet Union," Non-Destructive Testing, vol. 5, No. 3, pp. 154–159, Jun. 1972.

Dobbs et al.; "Generation of Ultrasonic Waves Without Using a Transducer," Non-Destructive Testing, vol. 4, No. 1, Feb. 1971, pp. 49–56.

Primary Examiner—Herbert Goldstein
Assistant Examiner—Stephen A. Kreitman
Attorney, Agent, or Firm—Joseph E. Rusz; Willard R. Matthews, Jr.

[57] ABSTRACT

A handheld, compact, self-contained transducer unit for electromagnetic generation and detection of ultrasound on or in metals and other media is realized by mounting short, flat cable sections directly on a small, powerful permanent magnet. The cable sections are interconnected in an electromagnetic transducer circuit configuration and the plane of the flat cable transducer circuit structure is perpendicular to the magnet magnetization axis. Fabrication of the device can be accomplished by selectively connecting the conductor ends of a flat strip electrical conductor segment and affixing the conductor segment to an appropriate surface of a samarium-cobalt permanent magnet.

1 Claim, 8 Drawing Figures

ELECTROMAGNETIC ULTRASOUND TRANSDUCER

STATEMENT OF GOVERNMENT INTEREST

The invention described herein may be manufactured and used by or for the Government for governmental purposes without the payment of any royalty thereon.

BACKGROUND OF THE INVENTION

This invention relates to acoustic wave electromagnetic transduction, and in particular to electromagnetic ultrasound transducers suitable for nondestructive testing applications.

Surface acoustic wave electromagnetic transducers (EMT's) which do not require contact with conducting materials for acoustic transduction, are being used particularly in applications for nondestructive testing and measurement of the physical properties of materials. The utility of these transducers has been somewhat restricted, however, by limitations of present fabrication techniques and by the lack of adequate information about their properties and spectral characteristics for design purposes.

Until quite recently most Rayleigh wave EMT's consisted of single or multiple windings of wire on various forms such as meander-line or grating patterns. Although frequencies up to several megahertz have been achieved by this method, the small-diameter wire required poses problems of difficult fabrication, resistive losses, spurious capacitive effects, poor uniformity, and mechanical fragility.

In contrast to wire-winding methods, excellent uniformity and high resolution can be systematically obtained by conventional photolithography. Thin-film aluminum meander lines deposited on silicon and quartz operating at 15 MHz, however, had large conductor resistance and high insertion losses. Recently, adequate flat conductor thicknesses have been achieved in meander-line EMT's made up to 4.75 MHz by the use of printed circuit board technology. Both the thin film and printing methods, however, require artwork (metallization or etching) skills and facilities.

There currently exists, therefore, a need for a device and method of fabrication that bypasses these requirements. It is desirable that such a device be inexpensive, small, lightweight and capable of conforming to any shape and that the method of fabrication be simple and utilize commercially available components. The present invention is directed toward satisfying such a need.

SUMMARY OF THE INVENTION

The invention comprises a small, compact, inexpensive, portable electromagnetic ultrasound transducer comprising a permanent magnet having a multiplicity of parallel flat strip conductors disposed along one magnet surface. The strip conductors are interconnected in an electromagnetic transducer circuit configuration and are in perpendicular relationship to the magnet magnetization axis. In a preferred embodiment the transducer is made from a short section of commercially available, flexible, multiconductor flat cable. The cable consists of parallel, flat, rectangular conductor bonded to a thin plastic backing or sandwiched between two plastic insulation layers. The conductor ends are soldered together so as to form a meander, grating, or other electromagnetic transducer circuit pattern.

It is a principal object of the invention to provide a new and improved electromagnetic ultrasound transducer.

It is another object of the invention to provide an electromagnetic ultrasound transducer that is small, compact, inexpensive and portable.

It is another object of the invention to provide an electromagnetic ultrasound transducer that can be readily fabricated using commercially available components.

It is another object of the invention to provide an electromagnetic ultrasound transducer that is easily manipulated and that has a flexible surface capable of conforming to test specimens of any shape.

It is another object of the invention to provide an electromagnetic ultrasound transducer having tailored beamshaping and improved frequency response characteristics.

These, together with other objects, features and advantages of the invention, will become more readily apparent from the following detailed description when taken in conjunction with the illustrative embodiments of the accompanying drawings.

DETAILED DESCRIPTION OF THE PREFERRED EMBODIMENT

Basic electromagnetic transducer (EMT) circuit geometries and design procedure are now well established.

Figure 1A:
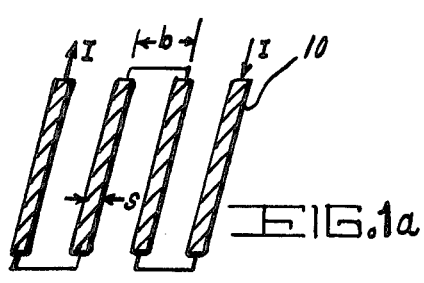
FIG. 1a illustrates a meander type EMT circuit geometry.
Figure 1B:
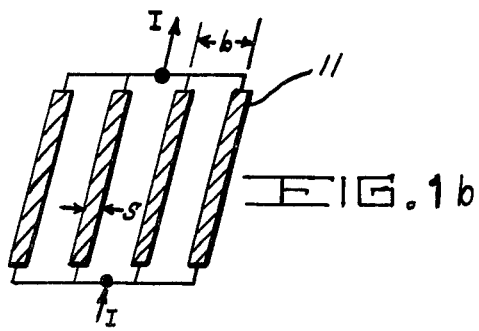
FIG. 1b illustrates a grating type EMT circuit geometry.

The two most common EMT circuit geometries are the meander line 10 and grating 11 shown in FIGS. 1(a) and (b), respectively. These arrays are made up of conductors flat or round (single or multiple windings) of length $l$, thickness $t$, and width S spaced at intervals of $b$. These transducers have a resonant frequency determined by their periodicity: $f_o = V/2b$ for the meander and $f_{oG} = V/b$ for the grating, where V is the velocity (Lamb wave or Rayleigh) of the sample. For transduction to occur, a static magnetic field is required. The main transduction mechanism is the action of periodic Lorentz forces on the sample surface. These transducers can be used in a noncontact mode in which Lorentz forces act on image eddy currents in a metal sample or a metal layer bonded to an insulator, or in a contact mode in which Lorentz forces act directly on transducer conductors bonded to an insulator.

Figure 2:
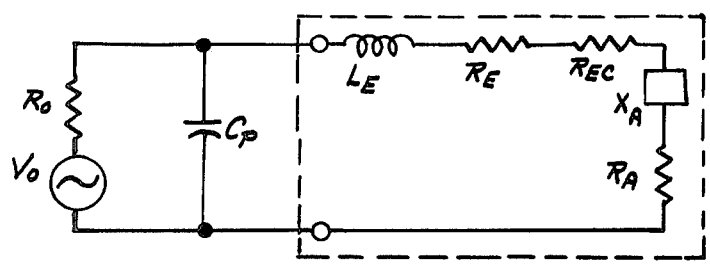
FIG. 2 is an equivalent circuit for an EMT with shunt capacitive matching.

The equivalent circuit for a noncontact SAW EMT is shown in FIG. 2. Here a source $V_o$ with impedance $R_o$ (50Ω), and shunt matching capacitor $C_p$ are connected to the transducer. The transducer consists of ordinary conductor resistance $R_E$; an inductance $L_E$ and an eddy current resistance $R_{EC}$, both gap dependent; and $R_A$ and $X_A$, acoustic radiation resistance and reactance, respectively. $L_E$ decreases as it approaches a metal sample surface, but $R_{EC}$, dependent on frequency and sample conductivity (zero for insulators), decreases with increasing gap from the surface.

The radiation resistance for a flat conductor meander configuration is (in MKS units)

$$R_A(\omega) = 2l\omega B_o^2 N^2 M^2 \operatorname{sinc}^2(S/2b) e^{-2\pi \bar{G}/b} \cdot \left| \operatorname{sinc} \left[ \frac{N(f - f_o)}{f_o} \right] \right|^2 \quad (1)$$

where $\omega$ is radian frequency, N is the number of transducer periods (2b), $\bar{G}$ is the mean gap measured from the sample surface to center of a transducer conductor, $M^2$ is a material parameter dependent on the orientation of $B_o$ and is described further later, and sinc (a) $\equiv$ sin(-$\pi$a)/$\pi$a. For transduction on insulators, $\bar{G}$ is effectively zero. When S/2b→0, this equation reduces to that of the small wire model at resonance.

For the grating, the corresponding expression is $$R_A(\omega) = 2l\omega B_o^2 \left( \frac{N_g}{2} \right)^2 M^2 \operatorname{sinc}^2 (S/b) e^{-4\pi \bar{G}/b} \cdot \left| \operatorname{sinc} \left[ \frac{N_G(f - f_{oG})}{f_{oG}} \right] \right|^2 \quad (2)$$

where $N_G$ is the number of periods (b) in the transducer.

For the usual shunt matched case depicted in FIG. 2, the EMT transduction efficiency is $$TE \approx \frac{2R_A/R_o}{\left( 1 + \frac{R_E + R_{EC}}{R_o} - \omega^2 L_E C_p \right)^2 + \left[ \frac{\omega L_E}{R_o} + \omega C_p (R_E + R_{EC}) \right]^2} \quad (3)$$

Also for the simple series matching case, TE is $$TE \approx \frac{2R_A/R_o}{\left( 1 + \frac{R_E + R_{EC}}{R_o} \right)^2 + \left[ 1/R_o \left( \omega L_E - \frac{1}{\omega C_S} \right) \right]^2} \quad (4)$$

The definition of single transducer insertion loss is 10 log TE. Transducer efficiency is reciprocal. These expressions include a factor of $\frac{1}{2}$ for the bidirectionality of the transducer. For a meander line, $R_A$ is typically microhms to milliohms. $R_E \sim$ several ohms, $R_{EC}° R_E$, and $L_E \sim$ a few microhenries or less.

Figure 3A:
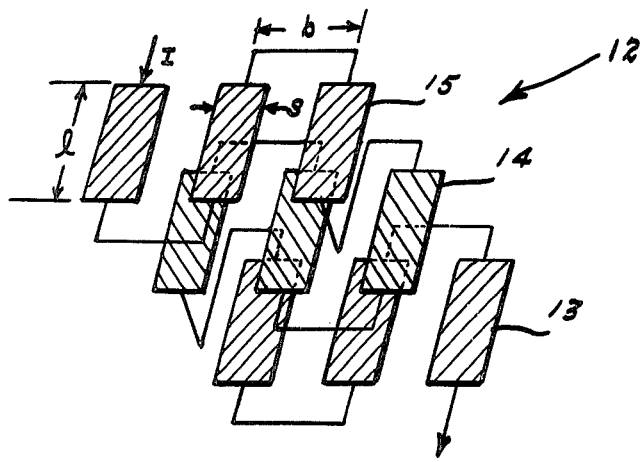
FIG. 3a illustrates a stacked configuration of three planar meander type circuits.
Figure 3B:
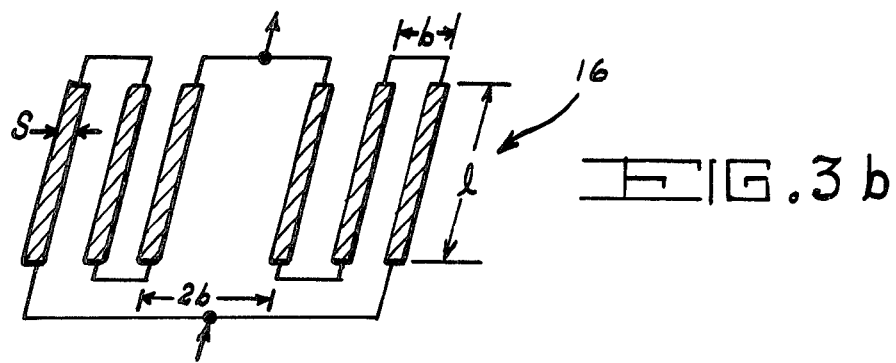
FIG. 3b illustrates a leakage minimizer configuration of two meander type circuit sections.

A very important consequence of these results is that the frequency response of these transducers, like that of interdigital transducers (IDT's) is simply determined by the number of periods, the bandwidth being about 1/N. Excellent agreement obtained with theory for transducer passbands demonstrates that transducer design is both straightforward and accurate. Furthermore, the frequency response is relatively insensitive to small changes in gap spacing even though the efficiency can be. The periodical article *Surface Acoustic Wave Electromagnetic Transducers From Multiconductor Flat Cable*, by H. M. Frost and T. L. Szabo, Applied Physics Letters, Vol. 29, No. 2, 15 July 1976, provides a more detailed consideration of the analytical design of meander lines. Two other meander-type geometries are shown in FIGS. 3a and 3b. The stacked transducer 12 of FIG. 3a is comprised of three planar meander line sections 13, 14, 15 aligned so that the currents in each stack flow in the same direction. A first-order estimate of effective current is to sum the contributions of each layer through simple addition. A three-layer transducer has been shown to be twice as efficient as a single layer EMT. The second configuration shown in FIG. 3b is for electromagnetic leakage minimization. In this case a balanced circuit transducer 16 is composed of two sections in parallel, and although it is less efficient acoustically than a usual meander having the same N, the leakage is reduced by about $-10$ dB relative to the acoustic signal.

As previously indicated, these electromagnetic transducer circuits must be used in combination with a static magnetic field.

With EMT's, the acoustic efficiency is greatest when the required magnetic field $B_o$ is parallel to the propagation direction on the test substrate. The magnet designs required to effect this parallelism, however, are magnetically quite inefficient (especially for nonferromagnetic substrates) because of marked flux leakage in the resulting magnetic circuit. The consequently large magnet and flux return core volumes and weights thus militate against the desired portability.

However, perpendicular fields can increase the magnetic efficiency (i.e., the ratio of useable magnetic flux to total flux) by orders of magnitude while the acoustic efficiency (TE) is typically reduced by only two or three. Such fields are easily obtained on a flat surface by resting on it the flat surface of a perpendicularly polarized bar magnet. These surface fields basically remain unchanged when a small but uniform gap is allowed for inserting the conductor pattern required for EMT operation. By using a short section of thin, multiconductor flat cable with flat (as opposed to round) conductors, it is possible to satisfy the conflicting requirements of small gap (to yield large (TE$\alpha B_o^2$) with reliable conductor pattern insulation (to avoid electrical shorting.)

Figure 4:
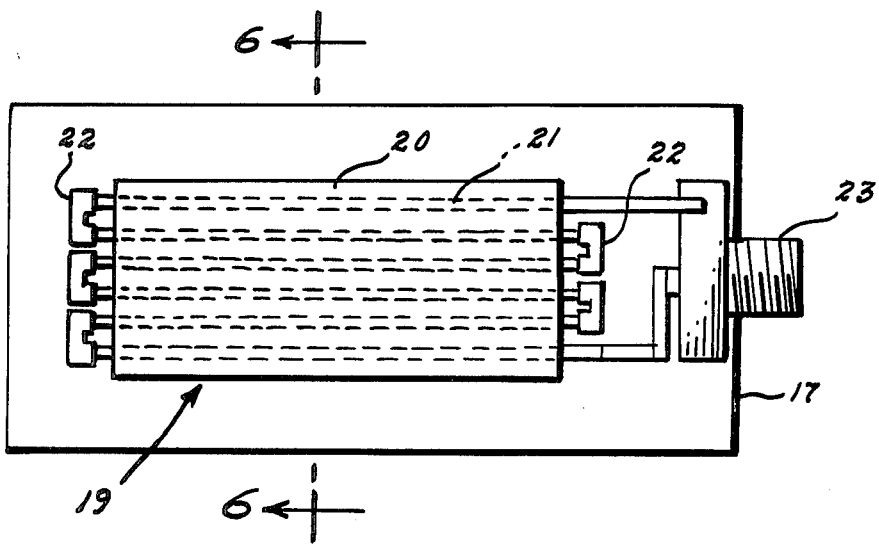
FIG. 4 is a plan view of one presently preferred embodiment of the invention.
Figure 5:
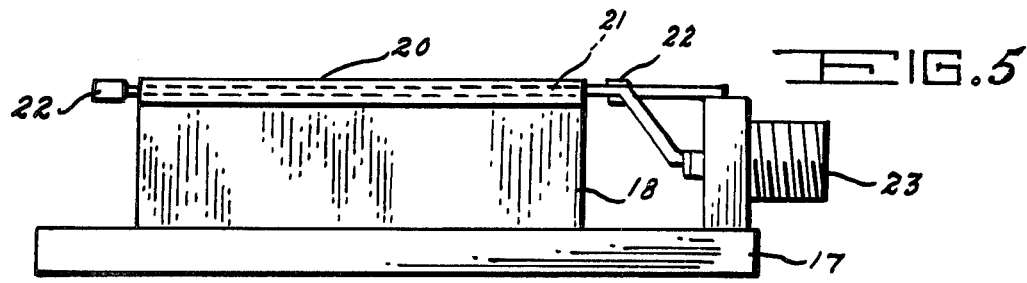
FIG. 5 is a view in elevation of the embodiment of FIG. 4.
Figure 6:
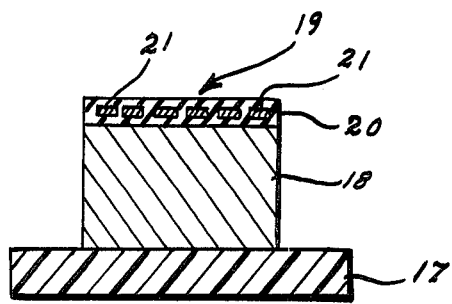
FIG. 6 is a sectional view of the embodiment of FIG. 4 taken at 3—3.

The embodiment of the invention illustrated by FIGS. 4–6 utilizes this approach. The transducer of FIGS. 4–6 comprises plastic base 17, samarium-cobalt permanent magnet 18 and multiconductor flat cable 19. Cable 19 is bonded to magnet 18 and its plane is perpendicular to the magnet's magnetization axis. Cable 19 consists of rectangular strip conductors 21 embedded in insulation 20. Conductors 21 are connected at their ends by connectors 22 to provide a continuous meander-type transducer circuit. Cable 19 can be a segment of commercially available multiconductor flat cable trimmed to leave the ends bare for the connections shown. This type cable can also be altered in many other ways to provide apodization, grating type circuits and other transducer circuit configurations. The circuit thus fabricated can be connected to a coaxial cable terminal 23 or other output device in a conventional manner.

Bonding the insulated cable surface to the adjoining magnet provides a self-contained unit. With both cable sides insulated, the EMT can be moved around at will (with standard lift-off) on the test substrate surface. With true contactless operation, the unbonded cable side can be bare. The magnets and electrical connectors are mounted on small plastic blocks as shown for structural integrity. Capacitive shunting provides good electrical matching.

In addition to the specific structure shown the invention also comprehends the use of: flexible magnets; magnets with curved surfaces; transducer apodization through change in cable envelope or magnet shape; flexible printed circuit and other conductor technologies; grating and other conductor patterns; bulk acoustic wave devices; techniques for bonding the EMT or conducting tape to nonconductors for transduction; cable connector technology; interchangeable magnets and conductor patterns; and programmable conductor patterns and shapes. Accordingly, although the invention has been described in one presently preferred embodiment, it is understood that the words which have been used are words of description rather than words of limitation, and that changes within the purview of the appended claims may be made without departing from the scope and spirit of the invention in its broader aspects.

What is claimed is:

1. An electromagnetic ultrasound transducer comprising the combination of
   a flexible permanent magnet,
   a plurality of flexible multiconductor flat cable segments, the several conductors of each said segment being interconnected to provide a meander type electromagnetic transducer circuit, said flat cable segments being stacked in a contiguous layered arrangement and interconnected to provide a single continuous meander transducer circuit having a terminal at each end thereof, the stack of cable segments being affixed to one surface of said magnet, the magnet magnetization axis being substantially perpendicular to the plane surfaces of said flat cable segments, and
   means for applying an alternating current signal to said transducer circuit terminals.

* * * * *